United States Patent [19]

Halm et al.

[11] Patent Number: 4,602,101

[45] Date of Patent: Jul. 22, 1986

[54] METHOD OF MANUFACTURING ALKYLHALOSILANES

[75] Inventors: Roland L. Halm, Madison, Ind.; Oliver K. Wilding, Jr., Louisville; Regie H. Zapp, Carrollton, both of Ky.

[73] Assignee: Dow Corning Corporation, Midland, Mich.

[21] Appl. No.: 797,372

[22] Filed: Nov. 12, 1985

[51] Int. Cl.$^4$ .............................. C07F 7/16; B01J 23/72
[52] U.S. Cl. ..................................... 556/472; 252/182
[58] Field of Search ......................... 556/472; 252/182

[56] References Cited

U.S. PATENT DOCUMENTS

| | | | |
|---|---|---|---|
| 2,380,995 | 8/1945 | Rochow | 556/472 |
| 2,380,996 | 8/1945 | Rochow et al. | 556/472 |
| 2,803,521 | 8/1957 | Nitzsche et al. | 556/472 X |
| 2,877,254 | 3/1959 | Enk et al. | 556/472 |
| 3,141,899 | 7/1964 | Emblem et al. | 556/472 |
| 4,314,908 | 2/1982 | Downing et al. | 252/182 |
| 4,500,724 | 2/1985 | Ward et al. | 556/472 |

FOREIGN PATENT DOCUMENTS 0178817  3/1966  U.S.S.R. .............................. 556/472

OTHER PUBLICATIONS

Bazant et al., "Angew-Chem. Int. Ed.", 7, No. 2, pp. 112-120, 1968.

*Primary Examiner*—Paul F. Shaver
*Attorney, Agent, or Firm*—Robert L. McKellar

[57] ABSTRACT

What is disclosed is a method of controlling a process for the preparation of alkylhalosilanes from silicon and alkylhalides where phosphorous or certain phosphorous compounds are used as promoters to enhance selectivity, overall yields of useable silanes and enhanced silicon metal conversion.

28 Claims, No Drawings

METHOD OF MANUFACTURING ALKYLHALOSILANES

BACKGROUND INFORMATION

This invention deals with a method of manufacturing alkylhalosilanes. More particularly, this invention deals with the use of phosphorous, certain phosphorous compounds or compounds that decompose to certain phosphorous compounds as promoters in the direct process for producing alkylhalosilanes. The benefits to be derived by the use of this invention can be increased alkylhalosilane yields, selectivity of certain alkylhalosilanes over other, less preferred alkylhalosilanes and, overall higher utilization of the raw materials used in the reaction mixture. In certain cases, using this invention, all three of these benefits can be had. In certain cases, using this invention, both the enhanced selectivity and the increased yields of alkylhalosilanes can be realized and, in certain other cases, the benefits of much higher conversion of raw materials to useable products is realized.

The Direct Process for producing alkylhalosilanes is well-known and has been refined and modified in many ways since Rochow first set forth the manner in which one could obtain alkylhalosilanes by contacting alkylhalides with silicon at elevated temperatures. The process is used for producing virtually all commercial alkylhalosilanes in the world today and Rochow's process was a significant deviation from the much more dangerous Grignard reaction for producing such silanes. Rochow in U.S. Pat. No. 2,380,995, issued Aug. 7, 1945 showed passing a gaseous stream of methylchloride into a heated tube where it contacted powdered silicon at about 300° C. Rochow obtained a mixture of silanes, most predominantly $CH_3SiCl_3$ and $(CH_3)_2SiCl_2$ at 52 and 14.5 weight percent respectively, to give a Me/Me$_2$ ratio (defined infra) of 3.6. It should be noted that Rochow also showed the passing of gaseous methylchloride over a powdered 50/50 by weight silicon-copper alloy and disclosed the use of metallic catalysts other than copper such as nickel, tin, antimony, manganese, silver and titanium, although the amounts and the physical forms of such catalysts are not disclosed by Rochow. Many silanes are formed by the Direct Process, such as, for example, tetramethylsilane, monomethyltrichlorosilane, silicon tetrachloride, trichlorosilane ($HSiCl_3$), methyldichlorosilane $MeHSiCl_2$, dimethylchlorosilane $\{(CH_3)_2HSiCl\}$, and trimethylchlorosilane $\{(CH_3)_3SiCl\}$. In modern manufacture, the largest volume silane manufactured is dimethyldichlorosilane as this silane constitutes the backbone of most high volume commercial silicone products after it has been hydrolyzed and condensed to the siloxane form. It is to the benefit of the manufacturer then to run the Direct Process to maximize the conversion of the raw materials to realize the highest yield of dimethyldichlorosilane. Thus, one of the principal objectives of the instant invention is to control the Direct Process to maximize the yield of dimethyldichlorosilane, i.e. to cause the process to be more selective in favor of dimethyldichlorosilane. A second objective of the instant invention is to maximize the overall yield from the raw materials. The more of the raw materials that are converted to silanes, the more economical is the process.

For purposes of this invention, the efficiency of converting raw materials is tracked by the amount of silicon metal charge that is converted to silane (% Si conversion). Those skilled in the art are particularly interested in the selectivity of the direct process reaction and for the purposes of this invention, this selectivity is indicated as the ratio of monomethyltrichlorosilane to dimethyldichlorosilane (Me/Me$_2$) in the crude reaction mixture. Sometimes, this ratio is also referred to as M/M$_2$ or T/D in the literature. An increase therefore, in the Me/Me$_2$ ratio, indicates that there is a decrease in the production of the more preferred dimethyldichlorosilane; conversely, a decrease in the ratio indicates that there is an increase in the production of the more preferred dimethyldichlorosilane.

When one considers that several millions of pounds of silanes are produced annually and consumed by the silicones commercial effort, it can be observed why small increments in selectivity, and raw material conversion are important to the manufacturer of silanes.

For example, assuming a manufacturer of silanes produces ten million pounds annually of silanes. If the process can be controlled to increase the overall yield of $(CH_3)_2SiCl_2$ by 2 or 3 percent, then the process becomes particularly attractive.

PRIOR ART

One major silicones producer was very active during the 1940's in working with the rudiments of the Direct Process and publishing the results. In addition to Rochow's '995 patent, these early researchers issued patents in order to arrive at the benefits discussed supra. Patnode, U.S. Pat. No. 2,380,997, issued August 7, 1945 dealt with the contact mass (charge) used in the Direct Process. The contact mass, initially disclosed by Rochow in the '995 patent, was treated by Patnode by molding the crushed silicon powder mass of Rochow, and subjecting it to a reducing atmosphere while firing it, in an effort to remove reducible components such as metallic oxides. Patnode also discloses the use of nickel, tin, antimony, manganese, silver, and titanium. The products were "especially useful" in preparing organosilicon halides.

Rochow and Gilliam, in U.S. Pat. No. 2,383,818, issued Aug. 28, 1945, disclosed the use of contact masses comprising silicon and an oxide of copper. Also included are copper compounds which are readily converted to the oxides, such as copper nitrate. The patent discloses enhanced efficiency of the contact mass, but overall yield, and the Me/Me$_2$ ratios are not disclosed. Shortly after Rochow and Gilliam's disclosure, U.S. Pat. No. 2,443,902 issued on June 22, 1948 to Ferguson and Sellers, wherein they disclosed, for the first time, an attempt to increase the yields of dialkylhalosilanes. The method comprised effecting reaction between an alkylhalide and silicon in the presence of a catalyst comprising a finely divided cupreous powder, the major portion of the particles of which are a few microns in size, and have as a principal constituent, friable metallic copper core particles surrounded by protective surface films of cuprous oxide, inhibiting oxidation in the air, said films being relatively thin as compared with the size of the enclosed copper cores. Using this technique, the inventors showed increased selectivity in favor of $(CH_3)_2SiCl_2$. Example 1, using the new material shows a crude yield of 48.7% with a Me/Me$_2$ ratio of 0.78. Example 2 showed an Me/Me$_2$ ratio of 0.18. Following on, Gilliam, in U.S. Pat. No. 2464033, showed, in addition to copper metal and oxides of copper, the use of copper halides as catalysts in the Direct Process. Further, this patent discloses the use of "promoters" such as zinc or zinc halides or their mixtures. Using such catalysts and promoters, Gilliam obtained overall yields of 42 to 99 percent but the selectivity in favor of $(CH_3)_2SiCl_2$ was not good, ranging from 0.20 to 0.48. This system will be generally compared to the instant invention by way of example, infra.

In another part of the World, other approaches were made to increase the conversion of raw materials into useful products and to control the direct process to give a uniform product. Nitzsche, in U.S. Pat. No. 2,666,775, disclosed the use of alloys of silicon with either copper or iron or both which were activated with chlorides of either copper, or iron, or both. The result was a Me/Me$_2$ ratio of 0.90. Sometime thereafter, Rossmy, in German patent 1165026, disclosed the use of silicon-copper alloys for the direct process, which alloys were doped with, among other elements, phosphorous, by sintering the dopant phosphorous with the finely ground silicon-copper alloy, in a stream of hydrogen, at temperatures in excess of 1000° C. More specifically, when ferrosilicon containing 95.5% silicon was sintered for three hours in a stream of hydrogen at 1030° C., with Cu$_3$Si, and with phosphorous, wherein the phosphorous content was 900 parts per million (ppm), and then reacted with $CH_3Cl \simeq 290°$ C., a reaction mixture was obtained containing 77.1% dimethyldichlorosilane having a Me/Me$_2$ ratio of 0.14. A comparison using no dopant gave 75.5% dimethyldichlorosilane and a Me/Me$_2$ ratio of 0.18. Special note should be taken of the manner in which the phosphorous was introduced into the reaction of the CH$_3$Cl and the silicon-copper mass.

In their treatise, "Synthesis of Organosilicon Monomers", A. D. Petrov, B. F. Mironov, V. A. Ponomarenko and E. A. Chernyshev, Consultants Bureau, New York, 1964, set forth a very extensive literature review on the direct synthesis of methylhalosilanes. They discuss the earlier Rochow work and the subsequent modifications, including those directed to the materials composed of copper and silicon. For example, page 32 of the treatise deals with the upper limit of copper in the copper/silicon contact mass and the all important use of copper salts as set forth by Rochow in U.S. Pat. No. 2,447,873 (1947) and British patent 626,519 (1948), as well as Nitzsche's two U.S. Pat. Nos. 2,666,775 and 2,666,776, and, the Russian authors Radosavievich, S. D. , Dragovich, M. D. Yachovich, M. S., in Glasnik Khem. Drushtva 21, 101 (1956). Further, the treatise makes reference to the additional use of Group VII metals (Nitzsche, German patent 921,566, 1954 and Kahlert, German patent 7651, 1955); zinc (Gilliam as set forth supra) and mercury (Japanese patent 5021, 1951).

From an abstract published in Soviet Inventions Illustrated, February, 1966, a method utilized by Trofimova et al. in an application No. 754,859 filed Dec. 8, 1961 (inventors certificate 122,749) it can be observed that phosphorous can be sintered with copper and silicon to form an alloy containing 150 to 250 ppm of phosphorous that can be used in the direct process to give 65% yields of dimethyldichlorosilane with an Me/Me$_2$ ratio of 0.30, at 310°–330° C. for eight hours.

In U.S. Pat. No. 3,446,829, issued May 27, 1969, Zock discloses the use of a cadmium promoter with a copper or silver catalyst and silicon in the direct process with the advantages of increased rate of reaction; increased selectivity for the formation of $(CH_3)_2SiCl_2$ and high silicon conversion rate.

Maas, et al. in U.S. Pat. No. 4,218,387, issued Aug. 19, 1980 describes the preparation of catalytic copper in terms of its particle size and copper oxide(I) content to give higher yields and greater selectivity. Maas also describes at column 3, lines 14–20, a small vibrating bed reactor (VBR) for the Direct process.

Ward, et al. in U.S. Pat. No. 4,487,950, describes the use of copper formate in conjunction with partially oxidized copper catalyst and particulated silicon. The advantage to be gained, as set forth by Ward, is the selectivity towards $(CH_3)_2SiCl_2$.

In another U.S. Pat. No., 4,500,724, Ward and coworkers disclose the use of tin as a co-catalyst with the catalyst of Rochow, namely copper and zinc, especially when the copper is in the form of copper chloride. Ward et al. claim that the reaction rate of the Direct process and product selectivity are achieved when attention is paid to the critical weight percent of copper relative to silicon and the critical weight ratios of tin and zinc are employed relative to copper. It will be shown in the examples how the use of phosphorous in Wards modified Direct process allows consistently higher yields overall; enhanced selectivity of $(CH_3)_2SiCl_2$ and higher conversion of the raw materials.

In U.S. Pat. No. 4,503,165, issued Mar. 5, 1985, Hashiguchi et al. disclose the use of hydroxides of Period IV metals, having atomic numbers between 24 and 30, as catalysts in conjunction with ground cupreous particulates and Schoepe and Hashiguchi in U.S. Pat. No. 4,504,596, issued Mar. 12, 1985, show the use of hydrated refractory oxides such as hydrated alumina for the same use, and finally, Hashiguchi et al. show elemental copper, cuprous and cupric oxides, in particulate form, for the preparation of alkyl and arylhalosilanes.

None of the above references show the use of elemental phosphorous, metal phosphides, or compounds that convert to metal phosphides under the Direct process conditions, as being useful in the Direct process when added to the Direct process at processing conditions. The inventors herein have found that phosphorous and phosphorous compounds when used as described infra, give enhanced overall yields; increased selectivity towards the formation of $(CH_3)_2SiCl_2$ and, the benefit of increased utilization of the raw materials in the Direct process for manufacturing alkylhalosilanes.

THE INVENTION

Pursuant to the above, the invention described herein comprises a method for controlling a process for the manufacture of alkylhalosilanes said process comprising, contacting an alkylhalide with metallurgical grade silicon, at a temperature of 250° C. to 350° C., in the presence of tin or tin compounds, and copper or copper compounds, wherein there is at least also present 25 to 2500 parts per million based on the silicon in the reaction mass, of a promoter selected from the group consisting of
  (I) elemental phosphorous;
  (II) metal phosphides and,
  (III) compounds capable of forming metal phosphides in the reaction mass of the process.

It has been found that the process herein can be any of those, in which the Direct Process as disclosed by Rochow in 1945, uses silicon and copper as long as there is also present tin, in some form, and phosphorous, as set forth hereinafter.

For example, the process can be that that is disclosed in U.S. Pat. No. 2,383,818 as long as there is also present tin and phosphorous as disclosed herein. The process, for example can be that set forth in U.S. Pat. No. 2,443,902 to Ferguson and Sellers, or that set forth in Gilliam in U.S. Pat. No. 2,464,033 using cupreous halides and oxides, or that set forth in Gilliam of also including zinc to give silicon, copper and zinc in combination, or that process set forth in Maas et al. in U.S. Pat. No. 4,218,387, or that set forth in Ward et al. in U.S. Pat. No. 4,487,950, using Copper Formate, or that process set forth in Ward et al. in U.S. Pat. No. 4,500,724 as long as there is also present tin and phosphorous as described in this invention, such processes and the disclosures associated therewith being incorporated herein by reference.

Thus, what is disclosed as the invention herein is a method for controlling a process for making alkylhalosilanes by contacting alkylhalides with silicon in the presence of copper, tin and phosphorous wherein the phosphorous is described infra.

The benefits to be derived by the use of this invention are enhanced overall yield; enhanced selectivity in favor of $(CH_3)_2SiCl_2$ and increased conversion of raw materials to useable products.

If one wishes to enhance the selectivity of the process to yield primarily $(CH_3)_2SiCl_2$, then a certain phosphorous compound can be selected and the amount utilized can be maintained to obtain such selectivity.

The alkylhalosilanes of the instant invention are those having the general formula (I) $R_nSiX_{4-n}$ and (II) $R_nH_mSiX_{4-n-m}$ with the former silanes being the preferred silanes of this invention. In the above formulae, each R is independently selected from alkyl groups of 1 to 4 carbon atoms and n has a value 1, 2 and 3 in formula (I) and n has a value of 1 or 2 in formula (II) and m in formula (II) has a value of 1 or 2, the sum of m+n cannot be greater than 3, and X is a halogen. Preferred silanes are those having the formula $R_2SiX_2$ and $RSiX_3$ wherein R is methyl or ethyl and X is chlorine. Most preferred is the silane $(CH_3)_2SiCl_2$.

Although methyl chloride is the preferred alkylchloride for this invention, other alkyl halides can be used, for example, ethyl, n-propyl and isopropylchlorides.

The silicon useful in this invention is any silicon having a purity of at least 95% by weight but less than 100% by weight of silicon. Most preferred is the metallurgical grade silicon having about 98% but less than 100% by weight of silicon. The silicon, for purposes of this invention can be particulated silicon or it can be particulated silicon/copper, whether in the form of discrete copper and discrete silicon particles or it can be a silicon/copper alloy which has been particulated.

The silicon or silicon/copper is fed into an appropriate reactor as needed. This process can be carried out under continuous conditions in a fluid bed, in a stirred bed reactor, fixed bed reactor or a batch mode, wherein the beds can be vibrated or not depending on the desired results. Preferred are the continuous modes of operation. Most preferred is a continuous fluidized bed operation.

The alkylhalide, or an inert gas such as argon, or mixtures thereof, can be utilized to fluidize the bed of particles in the reactor. The particles in the reactor can have average particle sizes ranging from greater than -0.1 micron to 800 microns, it being preferred to use particles having a size of 0.1 to 150 microns.

The process of this invention can be carried out at a temperature range of about 250° C. to 350° C. and it is preferred that the process be carried out in a range of 260° C. to 330° C. Most preferred is a temperature range of 280° C. to 320° C.

Generally, the components and reactants of the system, with the exception of the alkylhalide, are blended together in the reactor and heated to the reaction temperature and held for a short period of time. The alkylhalide, with or without the assistance of an inert gas, is fed into the reactor and the gaseous reaction products and the gaseous unreacted alkylhalide are passed through and removed from the reactor and trapped and then separated by distillation. Any particulate material flowing through the reactor with the effluent gases is also trapped and removed either to be recycled back to the reactor or discarded.

It is within the scope of this invention to utilize the apparatus of Dotson, U.S. Pat. No. 3,133,109, among others, to carry out the process of this invention, it being understood that the apparatus can be used as described by Dotson or it can be further modified by those skilled in the art to assist in the optimum selectivity and maximum amount of alkylchlorosilane obtainable. It should also be understood that purified alkylhalides are preferred for the inventive process but are not required. It should be further understood and appreciated that the treatment of the silicon particles, as set forth by Shade in U.S. Pat. No. 4,281,149 and the improvement disclosed by Shah et al. in U.S. Pat. No. 4,307,242, can be effectively used herein.

It would not be appreciated from the prior art that phosphorous can be utilized as an additive to the Direct Process to promote the formation of the alkylhalosilane as described herein in view of the teaching in the article by Lobusevich, et al. "Influence of Additions of Some Elements to Silicon-Copper Alloys on Their Activity in the Reaction With Methyl Chloride", Zhurnal Obshehei Khimu, Vol. 34, No. 8 pp 2706–2708, August, 1964, in which phosphorous, and sulfur, and beryllium are taught to be poisons for the reaction of siliconcopper alloys and methylchloride and in fact, the inventors herein have verified that teaching. The use of phosphorous without tin present, leads to increased selectivity i.e. increased levels of $(CH_3)_2SiCl_2$ but the reactivity or silicon conversion is significantly reduced. Thus there would be no motivation for the use of phosphorous by itself, or with tin in the Direct Process. The inventors herein, however, have found that in the presence of tin, phosphorous has a reverse effect on the results of the Direct Process.

Thus, aside from the silicon and copper required in the Direct Process, there is required by way of this invention, the presence of tin as a catalyst and phosphorous as a promoter in the reaction in order to obtain the benefits described herein. Useful in this invention as a catalyst or co-catalyst is tin in the form of alkyl tin halides, tetralkyltin, tin oxides, tin halides and tin metal dust.

Phosphorous which is critical to this invention as a promoter is elemental phosphorous, such as red phosphorous; metal phosphides and, phosphorous compounds which are capable of converting to metal phosphides under the reaction conditions involved in the formation of alkylhalosilanes prepared from silicon and alkylhalides as described supra.

Aside from elemental phosphorous, metal phosphides are useful in this invention. Such metal phosphides include, but are not limited to, for example, aluminum phosphide, calcium phosphide, copper phosphide, nickel phosphide, tin phosphide, and zinc phosphide, both $Zn_3P_2$ and $ZnP_2$, and iron phosphide, both $Fe_2P$ and $Fe_3P$ and silicon phosphide, wherein silicon as silicon phosphide is defined for purposes of this invention as a metal.

Also, aside from phosphorous and metal phosphides, included within the scope of this invention are compounds which convert to metal phosphides, as set forth within the scope of metal phosphides supra.

Such materials convert to metal phosphides under the reaction conditions in the Direct Process for the preparation of alkylhalosilanes, that is, they convert to metal phosphides in the presence of silicon, copper, and tin at 250° C. to 350° C.

Certain alloys are known to contain metal phosphides which are formed during the alloying process from the metals constituting the alloy and these materials are useful in this invention. Such materials are commercially available as can be evidenced by the information in the examples. Such materials are approximately 15% by weight phosphorous in copper principally as an alloy thereof and 7% by weight phosphorous in copper principally as an alloy thereof, the inventors not wishing to be held to any particular weight percent phosphorous therein as long as the amount of phosphorous required to be useful therein without using unduly large amounts of copper, is provided to the reactor.

The amount of phosphorous promoter useful herein ranges from 25 ppm to 2500 ppm calculated as phosphorous and is based on the amount of silicon used in the charge for the reactor.

The amount of tin used herein is critical and those amounts normally used in the Direct Process catalysts are those amounts intended for use herein. Thus, from 5 to 200 ppm based on silicon can be used herein without significantly detracting from the invention as described.

Thus, the phosphorous and tin along with silicon and copper and any other desirable materials can be introduced to the reactor as a contact mass by introducing the components separately or as a mixture, masterbatch, alloy or blend of two or more of the various components.

Another segment of this invention are the compositions useful in the Direct Process. Thus, this invention also consists of compositions of matter comprising metallurgical grade silicon; copper or copper compounds; tin or tin compounds and, phosphorous selected from the group consisting essentially of
 (I) elemental phosphorous;
 (II) metal phosphides and,
 (III) compounds capable of forming metal phosphides.

Aside from the silicon in the composition, there is present 0.2 to 10 weight percent copper; 5 to 200 parts per million tin and 25 to 2500 parts per million of phosphorous.

These components are based on the amount of silicon in the composition.

In addition, it is also beneficial that the compositions include aluminum, zinc and iron and therefore, there can be present, based on silicon, 100 to 10,000 parts per million zinc; 0.02 to 1 weight percent aluminum and up to 1 weight percent of iron.

Whenever the quantities of these ingredients are referred to herein, the quantities are based on the metal actually present in the compositions can be mixtures of all of such ingredients or mixtures of only some of the ingredients, as long as the compositions contain the required silicon, copper, tin and phosphorous.

Now so that those skilled in the art may understand and appreciate the instant invention, the following examples are provided. They are provided to illustrate the detailed points of the invention and they should not be construed as limiting the invention as it is set forth in the appended claims.

The reactor used for these examples is similar to that described in Maas, et al. U.S. Pat. No. 4,218,387 and is familiar to those skilled in the art for producing methylchlorosilanes using silicon and methylchloride. In general, the reaction is carried out by passing the methyl chloride, in vapor or gas form, over the surface of the silicon charge while maintaining the silicon charge at an elevated temperature. The heating of the reactant mixture is carried out, in this case, by immersing the reactor in a sand bath as a heat transfer medium.

The products of the reaction and any unreacted materials are condensed and collected in cold traps immersed in dry ice and alcohol. The products and unreacted materials are evaluated by gas chromatography by pouring the collected materials into cooled bottles (dry ice/isopropanol), cooling the chromatograph syringes and injecting samples into the gas chromatograph as quickly as possible.

The charge for the reactor is prepared by grinding silicon and shaking the ground silicon in a bottle for two or three minutes with any other solid ingredients desired to be included in the reaction. The charge is placed in the reactor and the reactor is closed and weighed to give initial charge weights. The gas flow for fluidization is started. The reactor is immersed in the sand bath. The receivers for the effluent are also weighed and then connected by tubes to the reactor. The reactor is heated by the sand bath and the bath is continuously fluidized to maintain close tolerances on the temperature.

The receiver (cold traps) are placed in the dry ice baths. After a few minutes the methylchloride flow to the reactor is started. After certain periods of time and at varying temperatures which are described in detail below, the methylchloride flow is terminated, and the receivers are disconnected and weighed prior to analysis. The reactor is removed from the sand bath after cooling and it is also weighed. This procedure is used essentially as described, throughout the examples herein.

For purposes of interpreting these examples and evaluating the results, the following apply:

$$\text{Me/Me}_2 \text{ ratio} = \frac{\text{Weight \% CH}_3\text{SiCl}_3}{\text{Weight \% (CH}_3)_2\text{SiCl}_2}$$

$$\% \text{ Si Conversion} = \frac{\cdot 100\% - \text{amount silicon left in the charge}}{\text{Total amount of silicon charged}}$$

EXAMPLE 1

Using the reactor described above, the following components were particulated, mixed together vigorously and fed to the reactor:
 100 parts Globe silicon, metallurgical grade, wherein 85% of the material has a particle size of less than 70 microns; (this silicon was used throughout the examples unless otherwise indicated);
 0.025 parts of zinc as powdered metal
 6.3 parts of cupreous chloride powder
 0.003 parts of tin as powdered metal and phosphorous in varying parts as shown in table I. Globe metallurgical silicon is available from Pickands Mather and Co., Cleveland, Ohio, U.S.A. and contains the following impurities:

| Compound | Amount (ppm) |
|---|---|
| iron | 5000 |
| aluminum | 3300 |
| calcium | 720 |
| titanium | 380 |
| vanadium | 110 |
| nickel | 70 |

The phosphorous used was a 15% by weight phosphorous-copper alloy purchased form Greenback Industries as product copper-phos lot number 1384. Greenback Industries is located in Greenback, Tennessee, U.S.A.

The reactor was closed and weighed and then placed in the sand bath at 315° C. Methylchloride was fed into the reactor. The reaction was continued for about 44 hours with all of the products and unreacted materials being trapped in the cold traps.

Throughout the examples, the additives were used in parts per million (ppm) based on the silicon present in the charge. The results for this example can be found on table I.

The $CH_3SiCl_3$ to $(CH_3)_2SiCl_2$ ratios set forth herein are those measured at the end of the 44 hour reaction time.

| | Results from Example 1 | | | | |
|---|---|---|---|---|---|
| Sample | Additive Amount (ppm) | Theory Phosphorous Added (ppm) | Weight % $(CH_3)_2SiCl_2$ | Me/ $Me_2$ | % Silicon Conversion |
| 1 | 2016 | 302 | 90.44 | 0.05 | 62.50 |
| 2 | 2500 | 375 | 91.26 | 0.05 | 40.10 |

EXAMPLE 2

A run was made essentially under the same reaction conditions as was used in example 1. The charge was: Globe silicon 100 parts; 6.3 parts of cuprous chloride; and 0.003 parts of tin metal. There was no zinc present. A phosphorous copper alloy as was used in example 1 was used herein. The results can be found on table II.

TABLE II

| | Non-Zinc Containing Charge | | | | |
|---|---|---|---|---|---|
| Sample | Additive Amount (ppm) | Theory Phosphorous Added (ppm) | Weight % $(CH_3)_2SiCl_2$ | Me/ $Me_2$ | % Silicon Conversion |
| 1 | 1521 | 228 | 77.51 | 0.13 | 75.78 |
| 2 | 1521 | 228 | 74.82 | 0.18 | 75.78 |

As a comparison, a run was carried out wherein there was no tin present in the reaction. As can be observed, the lack of tin did not allow an acceptable result. The charge was: 100 parts of Globe Silicon; 6.3 parts of cuprous chloride powder and; 0.025 parts zinc. The phosphorous was added as the 15% phosphorous-copper alloy. The results were:

| Sample | Additive Amount (ppm) | Theory Phosphorous Added (ppm) | Weight % $(CH_3)_2SiCl_2$ | Me/ $Me_2$ | % Silicon Conversion |
|---|---|---|---|---|---|
| 3 | 2000 | 300 | 76.48 | 0.16 | 15.36 |

EXAMPLE 3

Use of Aluminum Phosphide

In order to show that aluminum phosphide works in this invention, a charge was treated with aluminum phosphide prior to insertion into the reactor. The aluminum phosphide used was Aesar Powder, Lot 091484, purchased from Aesar Division, Johnson Matthey, Inc., Eagles Landing, P.O. Box 1087, Seabrook, New Hampshire 03874 U.S.A. Note the results on table III.

TABLE III

| | Aluminum Phosphide Additive | | | | |
|---|---|---|---|---|---|
| Sample | Additive Amount (ppm) | Theory Phosphorous Added (ppm) | Weight % $(CH_3)_2SiCl_2$ | Me/ $Me_2$ | % Silicon Conversion |
| 1 | 311 | 166 | 87.98 | 0.06 | 73.96 |
| 2 | 304 | 162 | 85.48 | 0.07 | 81.25 |

This data shows that by the use of aluminum phosphide, the selectivity of the reaction was enhanced to give more $(CH_3)_2SiCl_2$, the preferred product.

EXAMPLE 4

Use of Calcium Phosphide

In order to show the benefits of using calcium phosphide $(Ca_3P_2)$ in this invention, $Ca_3P_2$ was purchased from Alfa Products Division of Morton Thiokol, Inc. Damers, Mass. 01923 U.S.A. The $Ca_3P_2$ was used in the form of crushed lumps with the charge as set forth in example three, substituting the $Ca_3P_2$ for the aluminum phosphide. The results can be found on table IV.

TABLE IV

| | Calcium Phosphide | | | | |
|---|---|---|---|---|---|
| Run # | Additive Amount (ppm) | Theory Phosphorous Added (ppm) | Weight % $(CH_3)_2SiCl_2$ | Me/ $Me_2$ | % Silicon Conversion |
| 1 | 220 | 75 | 86.68 | 0.08 | 85.94 |
| 2 | 241 | 82 | 85.63 | 0.08 | 84.11 |
| 3 | 333 | 113 | 88.29 | 0.06 | 75.52 |
| 4 | 471 | 160 | 88.79 | 0.06 | 79.17 |
| 5 | 486 | 165 | 89.34 | 0.06 | 81.77 |
| 6 | 700 | 238 | 88.12 | 0.07 | 63.80 |
| 7 | 722 | 245 | 90.70 | 0.05 | 62.50 |
| 8 | 800 | 272 | 86.97 | 0.07 | 77.86 |
| 9 | 1096 | 373 | 92.03 | 0.04 | 52.34 |
| 10 | 1140 | 388 | 90.27 | 0.05 | 65.10 |
| 11 | 1187 | 404 | 90.91 | 0.05 | 82.55 |
| 12 | 1420 | 483 | 90.99 | 0.05 | 70.31 |
| 13 | 1556 | 529 | 89.25 | 0.06 | 71.88 |
| 14 | 1865 | 634 | 91.59 | 0.05 | 52.08 |
| 15 | 2044 | 695 | 88.94 | 0.07 | 32.55 |
| 16 | 2521 | 857 | 88.96 | 0.07 | 52.08 |
| 17 | 2737 | 931 | 90.00 | 0.07 | 43.49 |

This data shows both the increased yield and, selectivity regarding the $(CH_3)_2SiCl_2$ that can be obtained by the use of this invention.

EXAMPLE 5

Use of Cuprous Phosphide ($Cu_3P$)

In order to show the benefits of using $Cu_3P$ in this invention, $Cu_3P$, in the form of powder, was purchased from Alfa Products. Lot #26136 was used herein using the charge of example 3, substituting the aluminum phosphide by $Cu_3P$. The results can be found on Table V.

TABLE V

| | $Cu_3P$ | | | |
|---|---|---|---|---|
| Run # | Additive Amount (ppm) | Theory Phosphorous Added (ppm) | Weight % $(CH_3)_2SiCl_2$ | Me/ $Me_2$ | % Silicon Conversion |
| 1 | 349 | 49 | 79.45 | 0.11 | 54.71 |
| 2 | 541 | 76 | 80.02 | 0.11 | 58.85 |
| 3 | 667 | 93 | 89.41 | 0.06 | 60.68 |
| 4 | 975 | 137 | 82.92 | 0.10 | 32.55 |
| 5 | 1114 | 156 | 90.52 | 0.05 | 73.44 |
| 6 | 1117 | 156 | 90.37 | 0.05 | 77.86 |

EXAMPLE 6

Use of Cuprous Phosphide from a Second Source. ($Cu_3P$)

$Cu_3P$ was purchased in powdered form from Cerac, Inc. Milwaukee, Wisconsin 53201 U.S.A. and was identified as the −100 mesh powder. It was used along with the charge of example 3 by substituting the aluminum phosphide with $Cu_3P$. The results can be found on table VI.

TABLE VI

| | Cerac $Cu_3P$ | | | |
|---|---|---|---|---|
| Run # | Additive Amount (ppm) | Theory Phosphorous Added (ppm) | Weight % $(CH_3)_2SiCl_2$ | Me/ $Me_2$ | % Silicon Conversion |
| 1 | 180 | 25 | 88.94 | 0.05 | 71.88 |
| 2 | 180 | 25 | 86.51 | 0.07 | 53.91 |
| 3 | 992 | 139 | 89.43 | 0.05 | 56.77 |
| 4 | 1010 | 141 | 89.36 | 0.06 | 83.33 |

EXAMPLE 7

Use of Cuprous Phosphide from a Third Source ($Cu_3P$)

$Cu_3P$ was purchased in the form of pellets from ICN Pharmaceuticals, Inc., Life Sciences Group, KRK Labs, Plainview, NY 11803 U.S.A. The charge of example 3 was used, substituting crushed or ground $Cu_3P$ pellets for the aluminum phosphide. The results using the crushed pellets can be found on Table VII. The results using the ground pellets can be found on Table VIII.

TABLE VII

| | ICN Crushed Pellets $Cu_3P$ | | | |
|---|---|---|---|---|
| Run # | Additive Amount (ppm) | Theory Phosphorous Added (ppm) | Weight % $(CH_3)_2SiCl_2$ | Me/ $Me_2$ | % Silicon Conversion |
| 1 | 229 | 32 | 84.64 | 0.09 | 75.78 |
| 2 | 339 | 47 | 89.82 | 0.05 | 75.26 |
| 3 | 346 | 48 | 84.41 | 0.08 | 63.02 |
| 4 | 492 | 69 | 74.65 | 0.16 | 46.88 |
| 5 | 505 | 71 | 78.63 | 0.12 | 48.44 |
| 6 | 558 | 78 | 91.20 | 0.05 | 73.18 |
| 7 | 655 | 92 | 89.64 | 0.04 | 60.94 |
| 8 | 779 | 109 | 89.65 | 0.05 | 67.71 |
| 9 | 953 | 133 | 86.62 | 0.07 | 43.23 |
| 10 | 958 | 134 | 65.51 | 0.22 | 83.33 |
| 11 | 984 | 138 | 89.43 | 0.06 | 72.66 |
| 12 | 992 | 139 | 90.92 | 0.05 | 42.97 |
| 13 | 1008 | 141 | 89.41 | 0.06 | 90.89 |
| 14 | 1046 | 146 | 86.76 | 0.05 | 70.57 |
| 15 | 1052 | 147 | 87.33 | 0.07 | 62.24 |
| 16 | 1163 | 163 | 89.35 | 0.06 | 62.76 |
| 17 | 1052 | 147 | 88.41 | 0.06 | 84.11 |
| 18 | 1065 | 149 | 90.69 | 0.05 | 80.73 |
| 19 | 1171 | 164 | 90.60 | 0.08 | 69.01 |
| 20 | 1979 | 277 | 98.31 | 0.07 | 73.70 |
| 21 | 2042 | 286 | 90.53 | 0.06 | 77.60 |
| 22 | 2614 | 366 | 91.25 | 0.05 | 60.16 |

TABLE VIII

| | ICN Ground Pellets $Cu_3P$ | | | |
|---|---|---|---|---|
| Run # | Additive Amount (ppm) | Theory Phosphorous Added (ppm) | Weight % $(CH_3)_2SiCl_2$ | Me/ $Me_2$ | % Silicon Conversion |
| 1 | 984 | 138 | 89.43 | 0.06 | 80.73 |
| 2 | 1052 | 147 | 87.33 | 0.07 | 69.01 |
| 3 | 1052 | 147 | 88.41 | 0.06 | 73.70 |
| 4 | 1065 | 149 | 90.69 | 0.05 | 77.60 |

EXAMPLE 8

The Use of Phosphorous in the Form of a Copper/Phosphorous Alloy

Phosphorous, in the form of a copper-phosphorous alloy, which was ground to an average particle size of −325 mesh (ASTM Standard) was purchased from Greenback Industries, Greenback, Tennessee as #1384. This alloy contains about 15 weight percent phosphorous. Substituting the alloy for the aluminum phosphide and using the charge of example 3, two runs were run with lot #170, they are samples 9 and 10 and one sample was run with lot #119 (avg. 325 mesh powder) at the 1000 ppm level, sample 11. It should be noted that the sample 10 and 11 did not work as expected and higher levels are required for that particular material. Comparison should be made with sample 1 where 992 parts of powder worked but the result was not optimum. The results can be found on TABLE IX.

TABLE IX

| | 15% Phosphorous-Copper Alloy | | | |
|---|---|---|---|---|
| Run # | Additive Amount (ppm) | Theory Phosphorous Added (ppm) | Weight % $(CH_3)_2SiCl_2$ | Me/ $Me_2$ | % Silicon Conversion |
| 1 | 992 | 149 | 88.01 | 0.07 | 82.55 |
| 2 | 1513 | 227 | 91.47 | 0.05 | 78.65 |
| 3 | 1513 | 227 | 91.47 | 0.05 | 78.65 |
| 4 | 1513[1] | 227 | 93.08 | 0.04 | 79.43 |
| 5 | 1580 | 237 | 90.00 | 0.06 | 87.76 |
| 6 | 2000[2] | 300 | 90.04 | 0.05 | 76.82 |
| 7 | 2018 | 303 | 91.13 | 0.05 | 83.33 |
| 8 | 2500 | 375 | 90.96 | 0.05 | 78.13 |
| 9 | 1515 | 227 | 89.33 | 0.05 | 74.74 |
| 10 | 1521 | 228 | 84.61 | 0.10 | 85.94 |
| 11 | 1000 | 150 | 85.00 | 0.10 | 88.00 |

[1]Additional 500 ppm added at 20 hours
[2]Additional 577 ppm and 1.43 grams silicon @ 20 hours

EXAMPLE 9

Use of Phosphorous-Copper Alloy

A phosphorous-copper alloy was purchased from Metallurgical Products, Inc., West Chester, PA 19380 U.S.A. which was identified as % 15 copper-phosphorous alloy pellets. The charge of example 3 was used, substituting the crushed or ground P-Cu alloy for the aluminum phosphide. The results when the alloy was used in the ground form are given on TABLE X. The results when the alloy was used in the crushed form are given on table XI.

TABLE X

Metallurgical Phos./Cu Alloy Ground

| Run # | Additive Amount (ppm) | Theory Phosphorous Added (ppm) | Weight % $(CH_3)_2SiCl_2$ | Me/ $Me_2$ | % Silicon Conversion |
|---|---|---|---|---|---|
| 1 | 997 | 150 | 84.22 | 0.09 | 79.82 |
| 2 | 1078 | 162 | 85.14 | 0.09 | 87.24 |
| 3 | 2000 | 300 | 90.69 | 0.05 | 79.43 |
| 4 | 2000 | 300 | 88.76 | 0.06 | 78.13 |
| 5 | 2000 | 300 | 90.92 | 0.05 | 74.22 |
| 6 | 2500 | 375 | 90.44 | 0.05 | 83.07 |
| 7 | 2500 | 375 | 88.90 | 0.06 | 85.94 |

TABLE XI

Metallurgical Phos./Cu Alloy Crushed

| Run # | Additive Amount (ppm) | Theory Phosphorous Added (ppm) | Weight % $(CH_3)_2SiCl_2$ | Me/ $Me_2$ | % Silicon Conversion |
|---|---|---|---|---|---|
| 1 | 1000 | 150 | 86.30 | 0.08 | 82.29 |
| 2 | 1000 | 150 | 85.44 | 0.08 | 85.89 |
| 3 | 1016 | 152 | 81.87 | 0.11 | 86.46 |

EXAMPLE 10

Use of a Phosphorous-Copper Alloy Having a Lower Phosphorous Content

A phosphorous-copper alloy Product No. 25GO200TV was purchased from Baudier-Poudmet, 60140 Liancourt, France, which contained 7% phosphorous. Using the charge from example 3, but substituting the alloy of this example for the aluminum phosphide, this material was used in the powdered form. The results can be found on TABLE XII.

TABLE XII

Poudmet 7% Phos./Cu Alloy

| Run # | Additive Amount (ppm) | Theory Phosphorous Added (ppm) | Weight % $(CH_3)_2SiCl_2$ | Me/ $Me_2$ | % Silicon Conversion |
|---|---|---|---|---|---|
| 1 | 372 | 26 | 86.01 | 0.07 | 69.01 |
| 2 | 377 | 26 | 87.99 | 0.06 | 70.83 |
| 3 | 755 | 53 | 90.19 | 0.05 | 84.90 |
| 4 | 755 | 53 | 90.28 | 0.05 | 50.26 |
| 5 | 755 | 53 | 90.12 | 0.05 | 65.36 |
| 6 | 2396 | 168 | 89.57 | 0.05 | 83.59 |
| 7 | 2421 | 169 | 90.83 | 0.05 | 56.25 |
| 8 | 2487 | 174 | 91.93 | 0.04 | 41.93 |
| 9 | 4005 | 280 | 91.40 | 0.05 | 51.30 |
| 10 | 4010 | 281 | 92.51 | 0.04 | 84.11 |
| 11 | 5732 | 401 | 88.67 | 0.06 | 56.15 |
| 12 | 5747 | 402 | 88.12 | 0.06 | 81.77 |

EXAMPLE 11

Use of Red Phosphorous

Red phosphorous, purchased from Aesar Division of Johnson Matthy, Inc. having an average particle size of about −100 mesh powder (ASTM Standard), was used as the phosphorous additive in the charge of example 3 as a substitute for the aluminum phosphide. The results can be found on TABLE XIII.

TABLE XIII

Red Phosphorous

| Run # | Additive Amount (ppm) | Theory Phosphorous Added (ppm) | Weight % $(CH_3)_2SiCl_2$ | Me/ $Me_2$ | % Silicon Conversion |
|---|---|---|---|---|---|
| 1 | 139 | 139 | 87.76 | 0.07 | 83.33 |
| 2 | 150 | 150 | 89.54 | 0.05 | 77.86 |
| 3 | 232 | 232 | 89.26 | 0.07 | 86.98 |
| 4 | 255 | 255 | 89.71 | 0.05 | 76.82 |
| 5 | 475 | 475 | 91.65 | 0.05 | 48.96 |
| 6 | 662 | 662 | 90.33 | 0.06 | 44.01 |

EXAMPLE 12

Use of $Zn_3P_2$

Phosphorous, in the form of $Zn_3P_2$ was purchased from ICN in powder form. The material used in this example had the lot #88415X. When used according to this invention, using the charge of example 3 minus the aluminum phosphide, an improvement in the yield of $(CH_3)_2SiCl_2$ was realized along with an improved overall yield of silane materials. The results can be found in TABLE XIV.

TABLE XIV $Zn_3P_2$

| Run # | Additive Amount (ppm) | Theory Phosphorous Added (ppm) | Weight % $(CH_3)_2SiCl_2$ | Me/ $Me_2$ | % Silicon Conversion |
|---|---|---|---|---|---|
| 1 | 188 | 45 | 86.82 | 0.07 | 82.29 |
| 2 | 285 | 68 | 86.78 | 0.07 | 50.00 |
| 3 | 568 | 136 | 88.94 | 0.06 | 84.90 |
| 4 | 575 | 138 | 90.58 | 0.05 | 60.68 |

EXAMPLE 13

Use of $ZnP_2$

Phosphorous, in the form of $ZnP_2$, having an average particle size −100 mesh powder (ASTM Standard) was purchased from Cerac. When used according to this invention, with the charge of example 3 minus the aluminum phosphide, the results were as shown on TABLE XV.

TABLE XV $ZnP_2$

| Run # | Additive Amount (ppm) | Theory Phosphorous Added (ppm) | Weight % $(CH_3)_2SiCl_2$ | Me/ $Me_2$ | % Silicon Conversion |
|---|---|---|---|---|---|
| 1 | 330 | 161 | 87.97 | 0.06 | 56.25 |
| 2 | 333 | 162 | 87.89 | 0.06 | 83.07 |

EXAMPLE 14

Use of $NiP_2$ $NiP_2$ was substituted for the aluminum phosphide of example 3 with the results shown on TABLE XVI. The $NiP_2$ was purchased from Cerac, Inc., stock No. N-1044.

TABLE XVI

| Run # | Additive Amount (ppm) | Theory Phosphorous Added (ppm) | Weight % $(CH_3)_2SiCl_2$ | Me/Me$_2$ | % Silicon Conversion |
|---|---|---|---|---|---|
| 1 | 700 | 146 | 85.19 | 0.08 | 33.85 |
| 2 | 700 | 146 | 87.04 | 0.06 | 80.99 |
| 3 | 700 | 146 | 86.70 | 0.06 | 86.46 |
| 4 | 1400 | 293 | 86.70 | 0.05 | 63.02 |

EXAMPLE 15

Use of SnP

Tin phosphide was substituted for the aluminum phosphide of example 3. The results can be found on TABLE XVII. The tin phosphide was purchased from Aesar as catalog No. 12827.

TABLE XVII

SnP

| Run # | Additive Amount (ppm) | Theory Phosphorous Added (ppm) | Weight % $(CH_3)_2SiCl_2$ | Me/Me$_2$ | % Silicon Conversion |
|---|---|---|---|---|---|
| 1 | 26 | 5 | 78.68 | 0.13 | 66.67 |
| 2 | 28 | 6 | 80.64 | 0.12 | 78.65 |
| 3 | 312 | 65 | 77.71 | 0.16 | 63.54 |
| 4 | 607 | 126 | 82.03 | 0.13 | 44.01 |
| 5 | 612 | 127 | 76.92 | 0.17 | 39.06 |
| 6 | 1997 | 413 | 77.77 | 0.17 | 34.64 |
| 7 | 2000 | 414 | 76.26 | 0.20 | 34.90 |
| 8* | 20 | 4 | 86.01 | 0.07 | 58.59 |
| 9** | 49 | 10 | 82.27 | 0.09 | 79.69 |
| 10*** | 55 | 11 | 74.50 | 0.21 | 87.50 |

*Plus 14 ppm Sn
**No Sn in the standard reactor charge
***No Sn in the standard reactor charge

EXAMPLE 16

Use of FeP

Iron phosphide, in the form of a powder, was purchased from ICN as lot #23560 and used in the Direct Process, using the charge of example 3 minus the aluminum phosphide. The results are on TABLE XVIII.

TABLE XVIII

FeP

| Run # | Additive Amount (ppm) | Theory Phosphorous Added (ppm) | Weight % $(CH_3)_2SiCl_2$ | Me/Me$_2$ | % Silicon Conversion |
|---|---|---|---|---|---|
| 1 | 52 | 19 | 75.54 | 0.15 | 44.32 |
| 2 | 277 | 99 | 84.19 | 0.08 | 62.24 |
| 3 | 709 | 253 | 82.74 | 0.09 | 60.42 |
| 4 | 1979 | 707 | 82.73 | 0.10 | 34.11 |
| 5 | 2000 | 714 | 82.11 | 0.09 | 64.11 |

EXAMPLE 17

Use of Fe$_2$P

Iron phosphide in the form of 40 mesh powder, purchased form Cerac was substituted for the aluminum phosphide of example 3. The results can be found on TABLE XX.

TABLE XX

Fe$_2$P

| Run # | Additive Amount (ppm) | Theory Phosphorous Added (ppm) | Weight % $(CH_3)_2SiCl_2$ | Me/Me$_2$ | % Silicon Conversion |
|---|---|---|---|---|---|
| 1 | 722 | 151 | 86.00 | 0.07 | 67.45 |
| 2 | 767 | 160 | 86.79 | 0.07 | 75.52 |

EXAMPLE 18

Use of Fe$_3$P

Fe$_3$P, purchased form Cerac as 40 mesh powder was substituted for the aluminum phosphide of example 3. The results can be found on TABLE XXI.

TABLE XXI

Fe$_3$P

| Run # | Additive Amount (ppm) | Theory Phosphorous Added (ppm) | Weight % $(CH_3)_2SiCl_2$ | Me/Me$_2$ | % Silicon Conversion |
|---|---|---|---|---|---|
| 1 | 892 | 134 | 83.69 | 0.07 | 65.63 |
| 2 | 1006 | 151 | 81.42 | 0.10 | 72.92 |

EXAMPLE 19

Use of Silicon Phosphide

Silicon phosphide was purchased from Metron Incorporated, Allamrecky, New Jersey, U.S.A. and used in a powder form as a substitute for the aluminum phosphide of example 3. The results can be found on Table XXII.

TABLE XXII

SILICON PHOSPHIDE

| Run # | Additive Amount (ppm) | Theory Phosphorous (ppm) | Weight % $(CH_3)_2SiCl_2$ | Me/Me$_2$ | % Silicon Conversion |
|---|---|---|---|---|---|
| 1 | 55 | 29 | 81.3 | 0.11 | 89.58 |
| 2 | 58 | 30 | 84.98 | 0.08 | 63.28 |
| 3 | 319 | 167 | 80.78 | 0.10 | 57.03 |
| 4 | 354 | 186 | 85.74 | 0.07 | 50.78 |
| 5 | 792 | 415 | 84.50 | 0.08 | 65.89 |
| 6 | 876 | 459 | 83.02 | 0.10 | 86.72 |
| 7 | 1096 | 475 | 88.69 | 0.06 | 36.20 |
| 8 | 1103 | 578 | 84.47 | 0.09 | 33.85 |

EXAMPLE 20

Use of Silicon Phosphide

Silicon phosphide from example 19, was substituted for the aluminum phosphide of Example 3. In addition, the charge of silicon to the reactor did not contain any zinc. The results are shown on Table XXIII.

TABLE XXIII

SILICON PHOSPHIDE

| Run # | Additive Amount (ppm) | Theory Phosphorous (ppm) | Weight % $(CH_2)_2SiCl_2$ | Me/Me$_2$ | % Silicon Conversion |
|---|---|---|---|---|---|
| 1 | 300 | 157 | 81.0 | 0.12 | 52.6 |
| 2 | 300 | 157 | 81.5 | 0.11 | 48.4 |

EXAMPLE 21

Runs were carried out using a silicon purchased from a second source.

This example is included to show that the invention herein can be used with silicon from any source. Whereas the silicon used in the previous examples was Globe silicon, the silicon used in this example was obtained from A. S. Merakar Smelteverk, Koppera Norway and was used in powder form. The reactions were run at about 310° C. for 44 hours using the charge formula of example 1 except the silicon was substituted as indicated above. In table XXIV, the results are shown wherein runs 1 and 2 each contained Cu$^3$P and runs 3 to 6 contained no phosphorous. The silicon contained as impurities 2300 ppm aluminum; 1400 ppm of calcium; 3200 ppm of iron; 200 ppm of titanium and no detectable vanadium.

TABLE XXIV

| Run # | Additive Amount (ppm) | Theory Phosphorous (ppm) | Weight % $(CH_3)_2SiCl_2$ | Me/ Me$_2$ | % Silicon Conversion |
|---|---|---|---|---|---|
| 1 | 992 | 139 | 90.11 | 0.05 | 42.97 |
| 2 | 992 | 139 | 90.83 | 0.05 | 51.82 |
| 3 | 0 | 0 | 83.41 | 0.09 | 63.02 |
| 4 | 0 | 0 | 84.63 | 0.08 | 62.50 |
| 5 | 0 | 0 | 85.94 | 0.08 | 70.05 |
| 6 | 0 | 0 | 84.39 | 0.09 | 68.23 |

EXAMPLE 22

Runs were carried out using a silicon from a third source

The silicon used in this example was purchased from Pechiney Electrometallurgie, Paris-La-defense, France and was used in a powder form as in example 21 whereby the silicon was substituted as indicated. Runs 1 and 2 on Table XXV show the results using Ca$_3$P$_2$ while runs 3 and 4 show using 15% copper/phosphorous alloy and runs 5 to 7 do not contain any phosphorous. The silicon contained as impurities 2100 of ppm aluminum; 2600 ppm of calcium and 3700 ppm of iron.

TABLE XXV

| Run # | Additive Amount (ppm) | Theory Phosphorous (ppm) | Weight % $(CH_3)_2SiCl_2$ | Me/ Me$_2$ | % Silicon Conversion |
|---|---|---|---|---|---|
| 1 | 784 | 267 | 88.84 | 0.07 | 26.04 |
| 2 | 1248 | 424 | 89.84 | 0.07 | 33.33 |
| 3 | 1510 | 227 | 90.57 | 0.05 | 82.55 |
| 4 | 1518 | 228 | 89.58 | 0.06 | 88.54 |
| 5 | 0 | 0 | 84.17 | 0.08 | 38.68 |
| 6 | 0 | 0 | 81.14 | 0.10 | 37.76 |
| 7 | 0 | 0 | 85.21 | 0.08 | 39.58 |

EXAMPLE 23

Runs using a silicon from a fourth source

Silicon was purchased from Silicon Smelters (P.T.Y.) Ltd., Peitersburg 0700 So. Africa and used in the powdered from as in example 21 whereby the silicon was substituted as indicated. Runs 1 and 2 in Table XXVI used 15% copper/phosphorous alloy and runs 3 and 4 contained no phosphorous. The silicon contained as impurities 1500 ppm of aluminum; 300 ppm calcium; 1900 ppm of iron; 260 ppm of titanium and 120 ppm of vanadium.

TABLE XXII

| | SILICON PHOSPHIDE | | | | |
|---|---|---|---|---|---|
| Run # | Additive Amount (ppm) | Theory Phosphorous (ppm) | Weight % $(CH_3)_2SiCl_2$ | Me/ Me$_2$ | % Silicon Conversion |
| 1 | 1505 | 226 | 92.40 | 0.04 | 78.1 |
| 2 | 1529 | 229 | 91.53 | 0.05 | 83.6 |
| 3 | — | — | 84.60 | 0.09 | 60.2 |

TABLE XXII-continued

| | SILICON PHOSPHIDE | | | | |
|---|---|---|---|---|---|
| Run # | Additive Amount (ppm) | Theory Phosphorous (ppm) | Weight % $(CH_3)_2SiCl_2$ | Me/ Me$_2$ | % Silicon Conversion |
| 4 | — | — | 85.10 | 0.08 | 45.3 |

What is claimed is:

1. A method for controlling a process for the manufacture of alkylhalosilanes said process comprising, contacting an alkylhalide with metallurgical grade silicon, at a temperature of 250° C. to 350° C., in the presence of tin or tin compounds, and copper or copper compounds, wherein there is at least also present, 25 to 2500 parts per million based on the silicon in the reacton mass, of a promoter selected from the group consisting essentially of
   (I) elemental phosphorous;
   (II) metal phosphides and,
   (III) compounds capable of forming metal phosphides in the reaction mass of the process.

2. A method as claimed in claim 1 wherein the promoter is elemental phosphorous.

3. A method as claimed in claim 2 wherein the elemental phosphorous is white phosphorous.

4. A method as claimed in claim 2 wherein the elemental phosphorous is black phosphorous.

5. A method as claimed in claim 2 wherein the elemental phosphorous is red phosphorous.

6. A method as claimed in claim 1 wherein the promoter is a compound capable of forming metal phosphides in the reaction mass of the process.

7. A method as claimed in claim 6 wherein the promoter is a phosphorous-copper alloy.

8. A method as claimed in claim 1 wherein the promoter is a metal phosphide.

9. A method as claimed in claim 8 wherein the metal phosphide is aluminum phosphide.

10. A method as claimed in claim 8 wherein the metal phosphide is calcium phosphide.

11. A method as claimed in claim 8 wherein the metal phosphide is copper phosphide.

12. A method as claimed in claim 8 wherein the metal phosphide is nickel phosphide.

13. A method as claimed in claim 8 wherein the metal phosphide is tin phosphide.

14. A method as claimed in claim 8 wherein the metal phosphide is zinc phosphide.

15. A method as claimed in claim 1 wherein the alkylhalide is methylchloride.

16. A method as claimed in claim 1 wherein the process is carried out under continuous conditions in a fluid bed reactor.

17. A method as claimed in claim 16 wherein the bed is vibrated.

18. A method as claimed in claim 1 wherein the process is carried out in a stirred bed reactor.

19. A method as claimed in claim 1 wherein the process is carried out in a fixed bed reactor.

20. A method as claimed in claim 1 wherein the process is carried out in a batch mode.

21. A method as claimed in claim 1 wherein there is present, in addition to tin, copper and the phosphorous promoter, zinc.

22. A method as claimed in claim 21 wherein there is present, in addition to tin, copper, zinc and the phosphorous promoter, aluminum.

23. A method as claimed in claim 22 wherein there is present, in addition to tin, copper, zinc, aluminum and the phosphorous promoter, iron.

24. A composition of matter comprising metallurgical grade silicon; copper or copper compounds; tin or tin compounds and, phosphorous selected from the group consisting essentially of
   (I) elemental phosphorous;
   (II) metal phosphides and,
   (III) compounds capable of forming metal phosphides.

25. A composition as claimed in claim 24 wherein there is present metallurgical grade silicon;
   0.2 to 10 weight percent copper as copper;
   10 to 200 parts per million of tin as tin, and, 25 to 2500 parts per million of phosphorous as phosphorous all weights and parts based on the amount of silicon present in the composition.

26. A composition as claimed in claim 25 wherein there is also present 100 to 10,000 parts per million zinc as zinc, based on the amount of silicon present in the composition.

27. A composition as claimed in claim 26 wherein there is also present 0.02 to 1 weight percent aluminum as aluminum, based on the amount of silicon in the composition.

28. A composition as claimed in claim 27 wherein there is also present up to 1 weight percent of iron as iron, based on the amount of silicon present in the composition.

* * * * *